United States Patent
Kalas et al.

(10) Patent No.: US 6,755,775 B2
(45) Date of Patent: Jun. 29, 2004

(54) APPARATUS AND METHOD FOR LOADING A BRACHYTHERAPY SEED CARTRIDGE

(75) Inventors: Dan Kalas, Newhall, CA (US); David Bossi, Simi Valley, CA (US); L. Michael Cutrer, Chatsworth, CA (US)

(73) Assignee: North American Scientific, Inc., Chatsworth, CA (US)

( * ) Notice: Subject to any disclaimer, the term of this patent is extended or adjusted under 35 U.S.C. 154(b) by 0 days.

(21) Appl. No.: 09/943,168

(22) Filed: Aug. 30, 2001

(65) Prior Publication Data

US 2003/0045769 A1 Mar. 6, 2003

(51) Int. Cl.[7] .............................................. A61N 5/00
(52) U.S. Cl. ........................................................ 600/7
(58) Field of Search .................. 600/1–8; 604/97–100, 604/33, 57, 59, 60, 118, 533, 537, 539, 249; 89/34

(56) References Cited

U.S. PATENT DOCUMENTS

| | | | |
|---|---|---|---|
| 4,759,345 A | | 7/1988 | Mistry |
| 5,906,574 A | | 5/1999 | Kan |
| 6,007,474 A | * | 12/1999 | Rydell ............................. 600/7 |
| 6,102,844 A | * | 8/2000 | Ravins et al. .................... 600/8 |
| 6,213,932 B1 | * | 4/2001 | Schmidt ........................... 600/7 |
| 6,221,003 B1 | * | 4/2001 | Sierocuk et al. ................ 600/7 |
| 6,267,718 B1 | * | 7/2001 | Vitali et al. ..................... 600/7 |

FOREIGN PATENT DOCUMENTS

| | | | | |
|---|---|---|---|---|
| EP | 1072287 A2 | * | 1/2001 | ............ A61N/5/10 |
| WO | 0061229 | | 10/2000 | |
| WO | 2068052 A1 | | 9/2002 | |

* cited by examiner

Primary Examiner—Eric F. Winakur
Assistant Examiner—Nikita R Veniaminov
(74) Attorney, Agent, or Firm—Pillsbury Winthrop LLP

(57) ABSTRACT

The present invention relates to an apparatus and method for loading radioactive brachytherapy seeds into a seed cartridge for use with an applicator. Embodiments of the apparatus according to the present invention may include a number of contact points of a size and shape designed to conform to the main body of a brachytherapy seed. The apparatus may hold the seeds until the seeds are placed within a channel of the seed cartridge, at which point the seeds may be released from the contact sites by the application of a force to the seeds or by some other mechanism. The apparatus may be made from a flexible material so that the seeds may be released by the application of a tension force. According to embodiments of the method of loading the seed cartridge, seeds in the loader may be positioned in relation to the body of the loading apparatus and the ends of the seeds may be aligned with the channel of the seed cartridge. A seed may be placed in the channel so that a gripping portion of the loading device protrudes from an access portion of the channel. The apparatus may include gripping features so that the loading apparatus can be held firmly during the loading process.

16 Claims, 2 Drawing Sheets

APPARATUS AND METHOD FOR LOADING A BRACHYTHERAPY SEED CARTRIDGE

BACKGROUND

Radiation therapy is used in treating several medical ailments. In brachytherapy treatment, which is commonly used to treat various forms of cancer, "seeds" containing a radioactive isotope (e.g., iodine-125 or palladium-103) may be implanted in cancerous tissue. Exemplary seeds include the IoGold™ and PdGold™ seeds manufactured by North American Scientific, Inc. ("NASI") of Chatsworth, Calif. and marketed by Mentor Corporation of Santa Barbara, Calif., or the Prospera™ seed manufactured by NASI. During the active life of the isotope, the seeds, which are each smaller than a grain of rice, deliver a radiation dose to the surrounding tissue. The radiation pattern emitted by the seed depends upon the placement of the radioactive isotope within the seed, the seed housing material, the type of radioactive isotoped used and other factors. Depending upon the isotope used and the amount contained in a seed, the seed may emit radiation for weeks or months. Seeds are generally left in the patient when radiation emission has ceased due to isotope decay.

Prior to implantation the size and shape of the tissue to be irradiated may be mapped out using ultrasound or other imaging techniques. For example, an ultrasound imaging device may be used to image sections of a prostrate so that cancerous portions may be identified in each section. Together, these sections and a marginal area surrounding the cancerous tissue ("extracapsular region") may comprise the "target volume." The extracapsular region is tissue on the order of 2–5 millimeters thick that surrounds the prostate gland. Irradiating this region helps to ensure that cancer cells that may have migrated to the into the extracapsular region (i.e., "capsular extension") will also be treated.

Based on the resulting representation of the tissue, an optimized "dosimetry plan" for treatment of the target volume tissue may be developed. The dosimetry plan specifies the spatial distribution, number and dosage strength of seeds to be implanted. The dosimetry plan is developed with the goal of delivering the needed radiation dosage to the entire target region while ensuring that minimal non-target tissues are irradiated. A typical dosimetry plan may require that approximately one-hundred seeds be implanted.

Brachytherapy seeds are placed via needles which are inserted through the perineum into the prostate gland. Appropriate needle placement is determined base don the special distribution specified in the dosimetry plan and is executed using a guiding template or grid which is positioned in contact with the patient. Placement techniques of brachytherapy seeds vary, but generally, they are placed using preloaded needles, containing both seeds and inactive spacers, which position the seeds along a row in accordance with the dosimetry plan. A movable stylus is positioned within the needle against the column of seeds and spacers. The needle is then removed over the stylus, leaving the seeds and spacers in place. Alternatively, seeds can be placed using a mechanical applicator system, such as that available from Mick Radio-Nuclear Instrument, Inc. ("MRNI") of Mount Vernon, N.Y. The applicator system allows for individual seed placement without the use of inactive spacers.

Brachytherapy needles may come pre-loaded with brachytherapy seeds and inactive spacer elements or may be loaded at the hospital site prior to implantation. Loading individual seeds and spacers into a needle(s) can be laborious. Because the needle loading procedure can be lengthy and require close contact with the radioactive seeds, medical personnel are exposed to significant doses of radiation when loading the needles.

In the applicator system, one or more seed cartridges or "magazines" may supply seeds to a needle or multiple needles as necessary. Such needles include, for example, the MTP-1720-C or MTP-1820-C TP needles available from MRNI. MRNI also produces seed cartridges—Mick Magazines Catalog #7609 (reusable) and 7609 (disposable). These cartridges may contain up to fifteen seeds and are attached to the applicator. The applicator is fixed to a needle and is designed to place a single seed by ejecting it from the distal end of the needle, which has been placed in the prostate gland in accordance with the dosimetry plan. As a seed is placed, the physician positions the needle for the placement of other seeds. Users of applicator systems feel that such systems provide greater speed and control in the implantation process.

Disposable cartridges may come pre-loaded with seeds and may be made of a light plastic, while reusable cartridges may be made of a metal, such as stainless steel, that is suitable for sterilization in an autoclave. Because using disposable cartridges can be expensive, hospitals generally prefer to use reusable cartridges. While seed manufacturers are generally willing to pre-load single-use, disposable cartridges, they are usually unwilling to pre-load reusable cartridges because used cartridges may be tainted with bio-hazardous material and the handling of such material may require additional site safety certifications or pose additional hazards to employees.

Such reluctance often means that either medical personnel in the operating room or a third party contractor will be required to manually load the cartridge by placing individual seeds into a cartridge using a pair of tweezers or a hemostat. For an implantation procedure involving a hundred seeds, this loading process can be time-consuming and may expose the loading personnel to unnecessarily high doses of radiation, eliminating one of the advantages of using after-loading instead of pre-loaded needles. MRNI manufactures a "Seed Loading V-Block" (Catalog #7509) to assist in loading by holding a seed cartridge in place during the manual procedure. The V-Block comes with a gauge to measure seeds to ensure that they are the proper length (thereby avoiding jamming of the cartridge during loading). However, the task of manual loading remains tedious.

Moreover, because the seeds are small, they are easily lost if dropped during the loading process. Since the seeds are radioactive, medical personnel are required to find and properly dispose of any lost seeds, which is also a time-consuming process. Finally, improper loading of a cartridge may jam the cartridge, preventing its use.

For these reasons, there is needed a simple device and method for loading seeds into a seed cartridge that minimizes the radiation exposure to loading personnel and reduces the risk of dropped seeds or improper loading.

BRIEF DESCRIPTION OF THE DRAWINGS

FIG. 1C shows a cross-sectional front view of the seed cartridge as taken along line "I—I" in FIG. 1B.

DETAILED DESCRIPTION

Figure 1B:
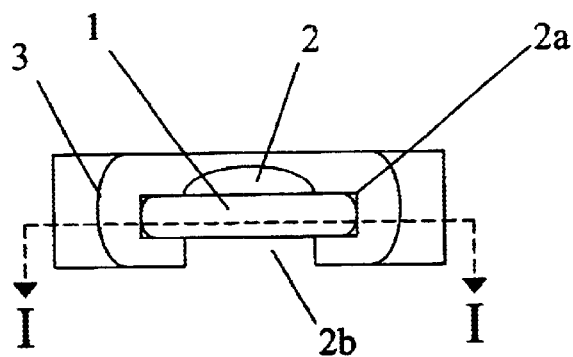
FIG. 1B shows a top view of the seed cartridge without loaded seeds.
Figure 1A:
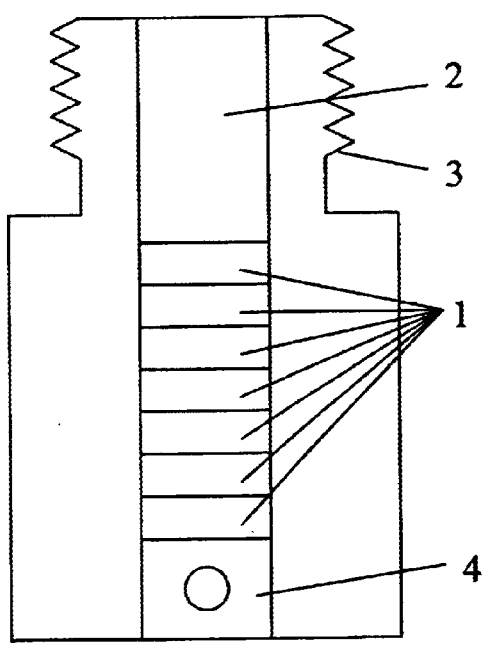
FIG. 1A shows a front view of a typical seed cartridge that may be loaded using embodiments of the present invention. The cartridge is shown loaded with brachytherapy seeds.
Figure 1C:
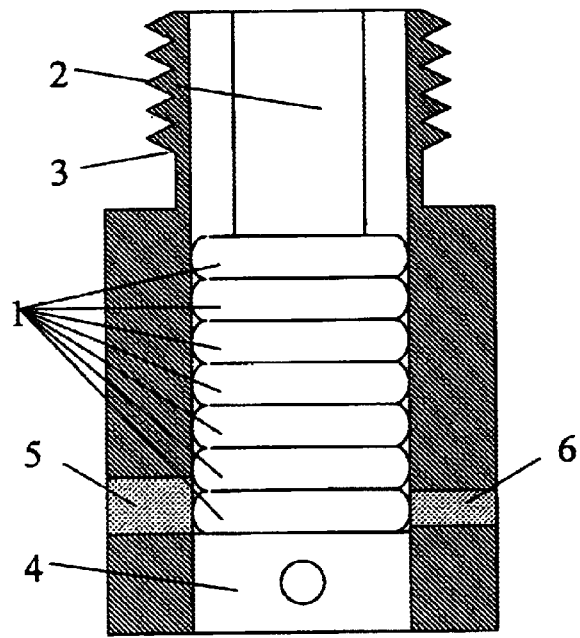
FIG. 1C depicts a cross-section of the loader as taken along line "I—I" in FIG. 1B.

The present invention relates to an apparatus and a method for loading a cartridge with brachytherapy seeds for use with a seed applicator. The cartridges may generally have a channel for containing the seeds FIGS. 1A–1C illustrate a typical seed cartridge that may be loaded by the apparatus of the present invention using the method of the present invention according to embodiments thereof. FIG. 1B shows a top view of the seed cartridge of FIG. 1A without loaded seeds so that the channel 2 can be more clearly seen. FIG. 1C is a cross-sectional view of the seed cartridge, the section being along the line "I—I" shown in FIG. 1B.

The seed cartridge is shown holding seven seeds 1 (although cartridges may be designed to hold greater or fewer seeds) in a stacked configuration within a channel 2. The seeds may have a cylindrical main body and rounded ends, as shown in FIG. 1A. Seeds of this shape include the IoGold™, PdGold™ and Prospera™ seeds manufactured by North American Scientific, Inc. of Chatsworth, Calif. Alternatively, the seeds 1 may have ends of a different shape (e.g., flat ends) or main bodies of a different shape (e.g., spherical). Such seeds may be loaded into cartridges having different channel shapes. Although the seeds 1 are shown in a stacked configuration, in other cartridges, seeds (including those with an elongated shape) may be placed end-to-end or in some other configuration that facilitates loading and/or unloading (feeding) of the seeds from the cartridge. Usually, a seed cartridge will be loaded with seeds of a uniform type (e.g., same radioactive isotope and dosage level) and shape, although a seed cartridge may also be loaded with a mixture of seeds using the device and method of the present invention.

The body of the seed cartridge may be made of stainless steel, a rigid plastic, or a similar material or combination of materials. The cartridge may have screw threads 3 that mate with threading in a port on the applicator (not shown) so that the cartridge may be securely attached to the applicator as seeds 1 are fed from the cartridge to the applicator for injection through an implantation needle. It is generally desirable that a rigid material be used to form these screw threads 3 so that the coupling between the cartridge and the port of the applicator is relatively fixed. Moreover, because the seeds 1 will be implanted, it is necessary to sterilize them. This is usually done at high temperatures in an autoclave. Accordingly, it is usually preferable that the body of the seed cartridge be made of a material that can withstand such temperatures. Finally, it may be preferable to construct the seed cartridge from a relatively radiopaque material so that minimal radiation is transferred from the seeds 1 to medical personnel handling the loaded seed cartridge during the sterilization and/or implantation procedure.

As shown in FIG. 1A, a stop 4 may block one end of the channel 2 to prevent the seeds 1 from passing through that end of the channel 2 as they are loaded into the other (open) end of the channel 2. When the loaded cartridge is mounted in the applicator, a spring-loaded plunger (not shown) may be inserted through the open end of the channel 2 so that the seeds are held in place. The type of cartridge shown in FIGS. 1A and 1B may have a seed outlet 5 which may be slightly larger in cross-section than the seeds 1. A corresponding opening 6 in the opposite wall of the cartridge may be smaller in cross-section than each of the seeds 1. A pin or other mechanism (not shown) may be inserted through the opening 6 and placed in contact with the seed 1 at the bottom of the stack (i.e., aligned with the seed outlet 5). The seed 1 at the bottom of the stack may be pushed through the seed outlet 5 and into the applicator by the pin or other mechanism.

In the cartridge shown in FIGS. 1A and 1B, the channel 2 has a chamber in which the seeds are stored (a "storage portion 2a") and a narrower groove that opens to the outer surface of the body of the seed cartridge (an "access portion 2b"). The storage portion 2a of the channel 2 may hold, for example, ten to fifteen seeds in a stacked configuration. The access portion 2b of the channel 2 may be sufficiently wide to allow the tips of a pair of tweezers or another gripping device to be inserted. Where the method of the present invention is not used and the seeds 1 are individually loaded, permitting the medical personnel loading the cartridge to guide the seeds 1 to the stack within the channel 2 may prevent jamming more effectively than if the seed is simply "dropped" at the open end of the channel 2.

Figure 2A:
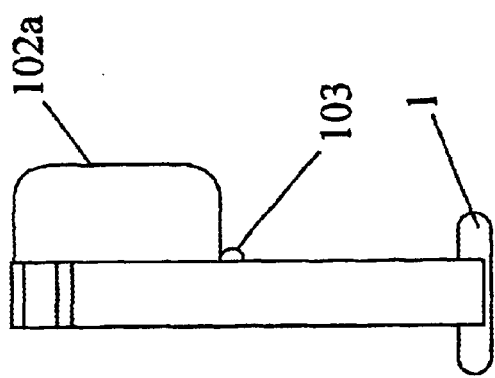
FIG. 2A shows a left side view of a loading apparatus according to an embodiment of the present invention. The loader is shown holding seven brachytherapy seeds.
Figure 2B:
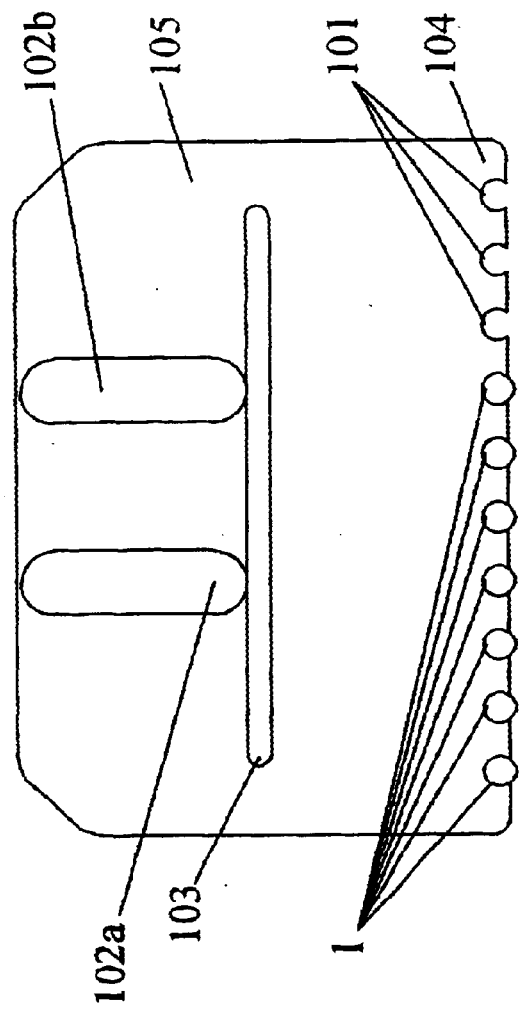
FIG. 2B shows a front view of the embodiment of the loading apparatus.
Figure 2C:
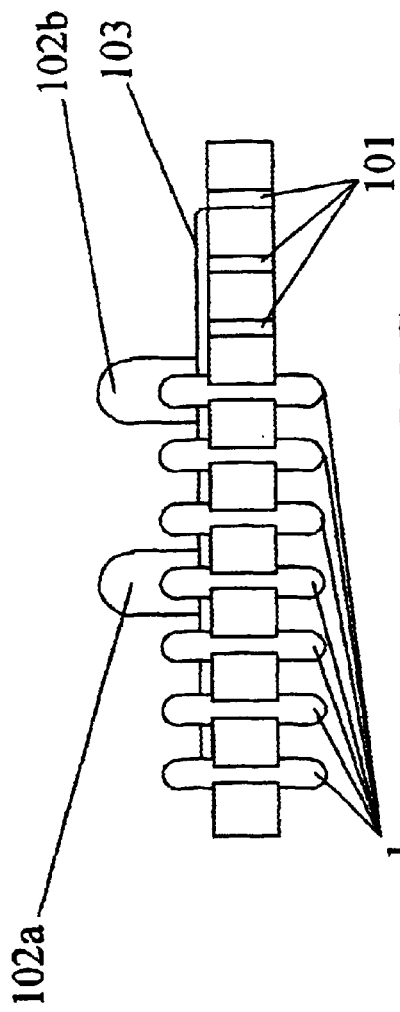
FIG. 2C shows a bottom view of the embodiment of the loading apparatus.

FIGS. 2A–2C depict an embodiment of an apparatus suitable for loading a seed cartridge like the one shown in FIGS. 1A–1C. The loading apparatus may have a carrier portion 104 with multiple contact sites 101 for holding the seeds 1. Seven of the contact sites 101 are shown holding seeds 1, while three of the contact sites 101 are shown without seeds 1. For clarity, only the contact sites 101 not holding a seed 1 are designated with the numeral "101" in FIGS. 2A–2C. The contact sites 101 may be shaped to conform to the shape of the main body of the seeds 1. For example, in the embodiment of the invention shown in FIGS. 2A–2C, the contact sites 101 may be rounded to conform to the cylindrical main bodies of the seeds 1. The contact sites 101 may be of a shape that is slightly more than half of a circle so that contact between the seeds 1 and the contact sites 101 can be maintained. The contact sites 101 may hold the seeds 1 in a pattern that corresponds to the configuration in which the seeds will be held when loaded into the channel 2 of the seed cartridge. For example, as shown in FIGS. 2A–2C, the seeds 1 are held parallel to each other to facilitate their loading into the channel 2 of the seed cartridge in a stacked configuration.

The body of the loader may be made of a flexible material, such as Santoprene, so that the seeds 1 may be removed from the contact sites 101 when force is applied to pull the seeds 1 out of the contact sites 101. The loader body material may also be chosen to be resistant to increased brittleness or rigidity when exposed to radiation, such as that emitted by the seeds 1. The width of the loader may be selected so that the loader can be inserted into the access portion 2b of the channel 2.

The loader may also have a grip portion 105 that can be gripped by a gripping device, such as a pair of tweezers or a hemostat, during the loading procedure. The grip portion 105 may have surface features that facilitate gripping the loader with such a gripping device. It may be particularly desirable to maintain a tight grip on the loader where the seed cartridge can easily be jammed by misalignment of the seeds 1 during loading. In the embodiment shown, one face of the loader has guides 102a and 102b and the other face has ridge 103. When gripping the loader with a pair of tweezers, for example, a user may place the end of the tweezer between the guides 102a and 102b to prevent the loader from slipping laterally or rotating while gripped. Similarly, many gripping devices have a notch shaped and sized to fit the seeds 1. To fit this notch, the loader may have a similarly sized ridge 103 to further prevent slipping or rotation of the loader. In FIGS. 2A–2C, the ridge 103 is shown on the opposite face of the loader's grip portion from the guides 102a and 102b. It will be readily understood by a person of ordinary skill in the art that, while embodiments of the apparatus are described above as having a carrier portion 104 and a grip portion 105, the loading apparatus may have a unitary body in which the carrier portion 104 and grip portion 105 are not physically divided (as shown in FIGS. 2A–2C).

The seeds 1 may be placed in contact with the contact sites 101 such that the seeds 1 are releasably held by the loader at the contact sites 101. The seeds 1 may be placed at the contact sites 101 during manufacture. In an embodiment in which the seeds 1 are held parallel to each other, the seeds 1 may be aligned so that their ends are the same distance from the body of the loader. Alignment may be performed at the point of manufacture or may be performed manually by the loading personnel, e.g., by pressing the ends of the seeds 1 against a flat surface. Once the seeds 1 are placed in contact with the contact sites 101, the loader may be gripped using a gripping device. For the embodiment of the loader shown in FIGS. 2A–2C and the seed cartridge shown in FIGS. 1A and 1B, the first seed 1 may be inserted into the storage portion 2a of the channel 2 such that the grip portion of the loader protrudes from the access portion 2b of the channel 2. This may be accomplished by holding the grip portion of the loader with a gripping device and orienting the loader so that the seeds 1 are aligned with the storage portion 2a of the channel.

The loader may be drawn downward so that successive seeds 1 are inserted into the storage portion 2a of the channel 2. Once the seeds 1 are in the storage portion 2a of the channel 2, they may be released from the contact sites 101 by pulling the loader out of the channel 2 so that the walls of the storage portion 2a of the channel exert force on the portion of the seeds 1 not in contact with the contact sites 101. In alternative embodiments, the seeds may be removed from the contact sites by, for example, applying force to an end of a seed 1 to cause it to slide out of contact with the contact sites 101. In other embodiments of the invention, the loader may have a mechanical release mechanism, such as a depressable release button, that may be activated to release the seeds 1. After the seeds are loaded into the seed cartridge, the seed cartridge is preferably sterilized.

The seed manufacturer may supply the customer with a seed loader holding seeds 1. The loader may be shipped in a container designed to maintain alignment of the seeds 1 in the loader in situations where the alignment of the seeds 1 is critical to proper loading (e.g., to prevent jamming of the channel 2). If the loader is made of a disposable material, the customer may simply dispose of the empty loader after the seeds have been loaded. Alternatively, the loader may be returned to the seed manufacturer for refilling. The loader may also be imprinted with a mark or code that indicates the type and/or dosage of seeds 1 held at the contact sites 101.

In embodiments of the invention, the pattern in which the seeds 1 are held in contact with the contact sites 101 may be longer than the channel 2. In such embodiments, only a part of the carrier portion of the loader may be contained in the storage portion 2a of the chamber 2. Thus, as the loader is drawn down through the channel, the bottom portion of the loader may be pulled out of the channel 2 as it comes against the stop 4 in order to allow the remaining portion of the loader to enter the chamber 2 through its open end. For such cases, it may be desirable that the loader be made of a flexible material so that the loader body to be bent around the stop 4.

In alternative embodiments of the invention, the carrier portion and grip portion of the loader may be arranged differently relative to each other. For example, in a strip-shaped embodiment of the invention, the carrier portion may have a number of contact sites arranged in a row and the grip portion may be positioned at one end of this row of contact sites.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A loading apparatus for loading a brachytherapy seed into a seed cartridge, said loading apparatus comprising:

a carrier portion having a contact site, said contact site releasably holding said brachytherapy seed; and a grip portion configure to be gripped by a gripping device as said brachytherapy seed is loaded into a seed channel in said cartridge, wherein said carrier portion is configured to be inserted into said seed channel such that said brachytherapy seed enters said seed channel through an open end of said seed channel, and said seed cartridge capable of storing a plurality of brachytherapy seeds and said carrier portion having a plurality of contact sites corresponding to a number of brachytherapy seeds that the seed cartridge is capable of storing.

2. The loading apparatus according to claim 1, said plurality of contact sites holding said plurality of brachytherapy seeds in a pattern corresponding to a configuration of brachytherapy seeds in said seed channel.

3. The loading apparatus according to claim 1, wherein said contact sites form a row and said grip portion is attached to said carrier portion proximate an end of said row.

4. An apparatus for loading a brachytherapy seed into a seed cartridge, said seed cartridge having a seed channel with an open end and holding said brachytherapy seed in a seed configuration in said seed channel, said loading apparatus comprising:

a carrier portion having a co tact site, said contact site releasably holding said brachytherapy seed; and a grip portion configured to the gripped by a gripping device as said brachytherapy seed is loaded into said seed cartridge, wherein said carrier portion is configured to be inserted into said seed channel such that said brachytherapy se d enters said seed channel through said open end, said grip portion having a first guide and a second guide, wherein said first guide and said second guide are configured so that the gripping device fits between said first guide and said second guide.

5. A loading apparatus for loading a brachytherapy seed into a seed cartridge, said loading apparatus comprising:
   a carrier portion having a contact site, said contact site releasably holding said brachytherapy seed; and
   a grip portion configure to be gripped by a gripping device as said brachytherapy seed is loaded into a seed channel in said cartridge, wherein
   said carrier portion is configured to be inserted into said seed channel such that said brachytherapy seed enters said seed channel through an open end of said seed channel, and said brachytherapy seed is released from said contact site when walls of a storage portion of the seed channel apply force to a portion of said brachytherapy seed not in contact with said contact site to pull said brachytherapy seed away from said carrier portion.

6. A loading apparatus for loading a brachytherapy seed into a seed cartridge, said loading apparatus comprising:
   a carrier portion having contact site, said contact site releasably holding said brachytherapy seed; and
   a grip portion configured to be gripped by a gripping device as said brachytherapy seed is loaded into a seed channel in said cartridge, wherein
   said carrier portion is configured to be inserted into said seed channel such that said brachytherapy seed enter said seed channel through an open end of said seed channel, and said brachytherapy seed is released from said contact site when walls of a storage portion of the seed channel apply force to an end of said brachytherapy seed so as to cause said brachytherapy seed to slide laterally relative to said carrier portion.

7. A loading apparatus for loading a brachytherapy seed into a seed cartridge, said loading apparatus comprising:
   a carrier portion having a contact site, said contact site releasably holding said brachytherapy seed; and
   a grip portion configured to be gripped by a gripping device as said brachytherapy seed is loaded into a seed channel in said cartridge, wherein
   said carrier portion is configured to be inserted into said seed channel such that said brachytherapy seed enters said seed channel through an open end of said seed channel, and said carrier portion is made of a radiation-resistant material.

8. A loading apparatus for loading a plurality of brachytherapy seeds into a seed cartridge, comprising:
   a carrier portion having a plurality of rounded contact sites, said contact sites being evenly spaced apart and each of said plurality of contact sites releasably holding one of said plurality of brachytherapy seeds; and
   a grip portion having a ridge corresponding to a notch in a gripping device and a first guide and a second guide that are spaced apart such that said gripping device fits between said first guide and said second guide, wherein each of said plurality of contact sites is rounded and is more than semicircular, and both said carrier portion and said grip portion are made of a flexible material.

9. A method of loading a brachytherapy seed into a seed channel of a seed cartridge, said brachytherapy seed having an end, and said seed channel having an open end, said method comprising:
   placing said brachytherapy feed into contact with a contact site of a loading device such that said brachytherapy seed is releasably held by said loading device at said contact site;
   positioning said end of said seed at a specified distance from said loading device;
   placing said brachytherapy seed into said seed channel through said open end; and
   releasing said brachytherapy seed from said contact site of said loading device, wherein releasing said brachytherapy seed from said contact site includes applying force to a part of said brachytherapy seed not in contact with said contact site, and applying force includes pulling said loading device out of said access portion of said seed channel, thereby pulling the part of said brachytherapy seed not in contact with said contact site against a lateral wall of said seed channel.

10. A method of loading a brachytherapy seed into a seed channel of a seed cartridge, said brachytherapy seed having an end, and said seed channel having an open end, said method comprising:
    placing said brachytherapy seed into contact with a contact site of a loading device such that said brachytherapy seed is releasably held by said loading device at said contact site;
    positioning said end of said brachytherapy seed at a specified distance from said loading device;
    placing said brachytherapy seed into said seed channel through said open end; and
    releasing said brachytherapy seed from said contact site of said loading device, wherein said seed channel has closed end blocked by a stop and said method including bending said loading device around said stop.

11. A method of loading a brachytherapy seed into a seed channel of a seed cartridge, said brachytherapy seed having an end, and said seed channel having an open end, raid method comprising:
    placing said brachytherapy seed into contact with a contact site of a loading device such that said brachytherapy seed is releasably held by said loading device at said contact site;
    positioning said end of raid brachytherapy seed at a specified distance from said loading device;
    placing said brachytherapy seed into said seed channel through said open end; and
    releasing said brachytherapy seed from said contact site of said loading device, further including gripping said loading device with a gripping device and orienting said loading device such that said brachytherapy seed is aligned with said seed channel.

12. A method of loading a brachytherapy seed into a seed channel of a seed cartridge, said brachytherapy seed having an end, and said seed channel having an open end, said method comprising:
    placing said brachytherapy seed into contact with a contact site of a loading device such that said brachytherapy seed is releasably held by said loading device at said contact site;
    positioning said end of said brachytherapy seed at a specified distance from said loading device;
    placing said brachytherapy seed into said seed channel through said open end;
    releasing said brachytherapy seed from said contact site of said loading device; and
    gripping said loading device with a gripping device and orienting said loading device such that said brachytherapy seed is aligned with said seed channel, wherein said loading device has a guide on a grippable surface, and gripping said loading device includes placing a of said gripping device against said guide.

13. A method of loading a brachytherapy seed into a seed channel of a seed cartridge, said brachytherapy seed having an end, and said seed channel having an open end, said method comprising:

placing said brachytherapy steed into contact with a contact site of a loading device such that said brachytherapy seed is releasably held by said loading device at said contact site;

positioning said end of said brachytherapy seed at a specified distance from said loading device;

placing said brachytherapy seed into said seed channel through said open end;

releasing said brachytherapy seed from said contact site of said loading device; and gripping said loading device with a gripping device and orienting said loading device such that said brachytherapy seed is aligned with said seed channel, wherein loading device has a ridge on a grippable surface, and said gripping device has a notch, and further wherein gripping said loading device includes placing said ridge within said notch.

14. The method according to claim 13, wherein said ridge is of substantially the same shape as said seed and wherein said notch has a shape corresponding to the shape of said seed.

15. A method of loading a brachytherapy seed into a seed channel of a seed cartridge, said brachytherapy seed having an end, and said seed channel having an open end, said method comprising:

placing said brachytherapy seed into contact with a contact site of a loading device such that said brachytherapy seed is releasably held by said loading device at said contact site;

positioning said end of said brachytherapy seed at a specified distance from said loading device;

placing said brachytherapy reed into said seed channel through said open end;

releasing said brachytherapy seed from said contact site of said loading device; and gripping said loading device with a gripping device and orienting said loading device such that said brachytherapy seed is aligned with said seed channel, wherein said gripping device is one of a air of tweezers and a hemostat.

16. A method of loading a plurality of brachytherapy seeds into a seed channel of a seed cartridge, comprising:

placing each of said plurality of brachytherapy seeds in contact with one of a plurality of contact sites of a loading device, said loading device having a carrier portion and a grip portion, and said grip portion having a first guide, a second guide, and a ridge;

positioning said plurality of brachytherapy seeds such that an end of each of said plurality of brachytherapy seeds is at a uniform distance from a corresponding one of said plurality of contact sites;

placing a portion of a gripping device between said first guide and said second guide, said gripping device having a notch;

placing said ridge within said notch of said gripping device;

gripping said grip portion of said loading device;

orienting said loading device such that said plurality of brachytherapy seeds are aligned with a storage portion of said channel;

placing at least one of said plurality of brachytherapy seeds within said seed channel such that said rip portion of said loading device protrudes through access portion of said seed channel; and applying a tension force to aid grip portion of said loading device such that said at least one of said plurality of brachytherapy seeds placed within said seed channel is released from the corresponding one of said plurality of contact sites.

* * * * *